United States Patent [19]
Nguyen et al.

[11] Patent Number: 5,931,817
[45] Date of Patent: Aug. 3, 1999

[54] PEN NEEDLE ASSEMBLY

[75] Inventors: Tuan V. Nguyen, Rockaway; Michael A. DiBiasi, West Milford; Robert E. West, Morristown, all of N.J.

[73] Assignee: Becton Dickinson and Company, Franklin Lakes, N.J.

[21] Appl. No.: 08/928,274

[22] Filed: Sep. 12, 1997

[51] Int. Cl.⁶ ..................................................... A61M 5/00
[52] U.S. Cl. .......................................... 604/263; 604/192
[58] Field of Search .................................... 604/192, 199, 604/200, 201, 205, 206, 239–244, 256, 263, 283, 403, 411–414, 905

[56] References Cited

U.S. PATENT DOCUMENTS 4,976,701  12/1990  Ejlersen et al. ........................ 604/192
5,250,037  10/1993  Bitdinger ................................ 604/242
5,549,575  8/1996  Giambattista et al. ................. 604/206
5,611,785  3/1997  Mito et al. ............................. 604/240

*Primary Examiner*—John D. Yasko
*Attorney, Agent, or Firm*—Alan W. Fiedler

[57] ABSTRACT

A pen needle having a cylindrical hub including a distal section that is received in a needle holder and a proximal section having threads that mate with a pair of lugs in an adaptor mounted on a medication delivery pen. The distal end of the pen needle includes a plurality of splines that mate with splines in the needle holder to prevent the pen needle from rotating within the needle holder and aid in threading the pen needle onto the adaptor. The pen needle is fully received in the needle holder to shield the proximal point of the pen needle and can only be removed from the needle holder by using the adaptor or a cartridge retainer having the proper pair of lugs thereon.

8 Claims, 6 Drawing Sheets

PEN NEEDLE ASSEMBLY

BACKGROUND OF THE INVENTION

1. Field of the Invention

The subject invention relates to a pen needle assembly and, more particularly, to a pen needle that attaches to a medication delivery pen using a reverse Luer-lock.

2. Description of Related Art

Hypodermic syringes are used to deliver selected doses of medication to patients. The prior art hypodermic syringe includes a syringe barrel having opposed proximal and distal ends. A cylindrical chamber wall extends between the ends and defines a fluid receiving chamber. The proximal end of the prior art syringe barrel is substantially open and receives a plunger in sliding fluid tight engagement. The distal end of the prior art syringe barrel includes a passage communicating with the chamber. A needle cannula is mounted to the distal end of the prior art syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior art hypodermic syringe often is stored in a vial having a pierceable elastomeric seal. Medication in the prior art vial is accessed by piercing the elastomeric seal with the needle cannula. A selected dose of the medication is drawn into the chamber of the syringe barrel by moving the plunger a selected distance in a proximal direction. The needle cannula is withdrawn from the vial, and the medication is injected into a patient by moving the plunger in a distal direction.

Some medication, such as insulin is self-administered. The typical diabetes patient will require injections of insulin several times during the course of the day. The required dose of insulin will vary from patient to patient, and for each patient may vary during the course of the day and from day to day. Each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard prior art hypodermic syringe and vial can be inconvenient and embarrassing in these public environments.

Medication delivery pens have been developed to facilitate the self-administration of medication. One prior art medication delivery pen includes a cartridge holder into which a cartridge of insulin or other medication may be received. The cartridge holder is an elongate generally tubular structure with proximal and distal ends. The distal end of the prior art cartridge holder includes mounting means for engaging a double-ended needle cannula. The proximal end also includes mounting means for engaging a driver and dose setting apparatus as explained further below. A disposable cartridge for use with the prior art cartridge holder includes a distal end having a pierceable elastomeric seal that can be pierced by one end of a double-ended needle cannula. The proximal end of this prior art cartridge includes a plunger slidably disposed in fluid tight engagement with the cylindrical wall of the cartridge. This prior art medication delivery pen is used by inserting the cartridge of medication into the cartridge holder. A prior art pen body then is connected to the proximal end of the cartridge holder. The pen body includes a dose setting apparatus for designating a dose of medication to be delivered by the pen and a driving apparatus for urging the plunger of the cartridge distally for a distance corresponding to the selected dose.

The user of the pen mounts a prior art double-ended needle cannula to the distal end of the cartridge holder such that the proximal point of the needle cannula pierces the elastomeric seal on the cartridge. The patient then selects a dose and operates the pen to urge the plunger distally to deliver the selected dose. The dose selecting apparatus returns to zero upon injection of the selected dose with this prior art medication delivery pen. The patient then removes and discards the needle cannula, and keeps the prior art medication delivery pen in a convenient location for the next required medication administration. The medication in the cartridge will become exhausted after several such administrations of medication. The patient then separates the cartridge holder from the pen body. The empty cartridge may then be removed and discarded. A new cartridge can be inserted into the cartridge holder, and the cartridge holder and pen body can be reassembled and used as explained above.

The above described medication delivery pen is effective and much more convenient for self-administration of medication than the typical hypodermic syringe and separate medication vial. However, after using the prior art double-ended pen needle the user was required to take care in disposing of the pen needle to prevent an accidental needle stick and the storage of unused needles and the final disposal of used needles has presented problems. In particular, supplies of new needles often are loosely scattered in the bottom of purses or briefcases, and used needles are often disposed of unsafely.

SUMMARY OF THE INVENTION

The subject invention relates to a pen needle assembly for use with medication delivery pens. The pen needle assembly of the present invention is used with an adaptor that is threaded onto a conventional medication delivery pen. The pen needle assembly includes a pen needle having a hub having a cannula mounted therein, with a distal point and a proximal point. The proximal end of the hub includes a set of threads designed to attach the hub of the pen needle to the adaptor and the distal end of the hub includes a plurality of splines that mate with matching splines in a needle holder or cavity to prevent the pen needle from rotating with respect to the cavity when the pen needle is being mounted on or taken off the adaptor.

In addition, the pen needle is designed to be fully received in the needle holder to shield the proximal point of the pen needle from contact and only removed from the needle holder by using an adaptor or medication delivery pen having a special pair of lugs thereon.

These and other aspects, features and advantages of the present invention will become apparent from the following detailed description taken in conjunction with the accompanying drawings.

DETAILED DESCRIPTION

Figure 1:
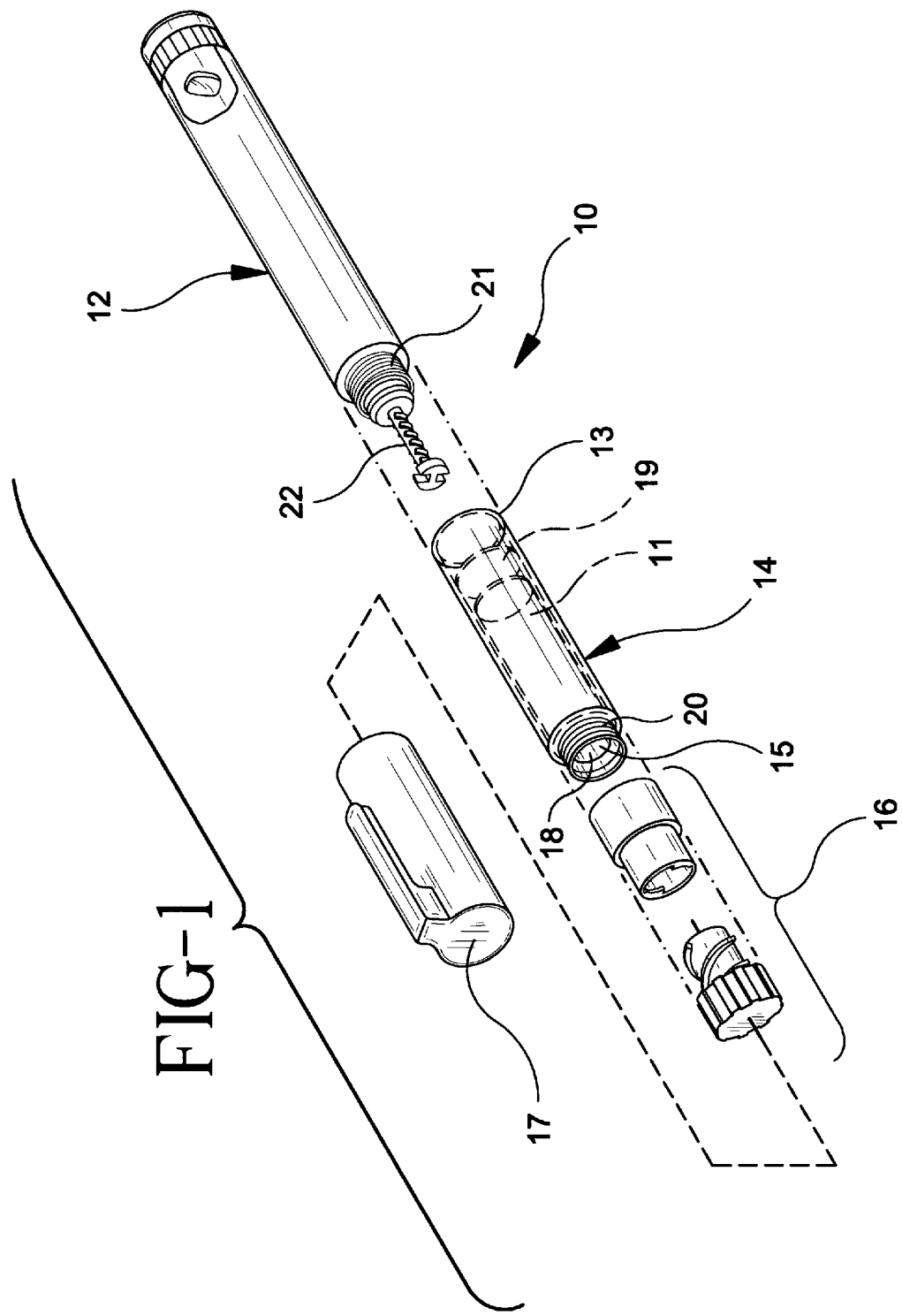
FIG. 1 is an exploded perspective view of a medication delivery pen including an adaptor and pen needle assembly according to the present invention.

FIG. 1 is an exploded perspective view of a medication delivery pen 10 including an adaptor and pen needle assembly 16, according to the present invention. As shown in FIG. 1, medication delivery pen 10 contains a cartridge 11 having sufficient medication for several doses. A distal end of cartridge 11 is closed by a pierceable and resealable rubber septum identified by the numeral 18 and a proximal end of cartridge 11 receives a stopper 19 in sliding fluid-tight engagement with cartridge 11. Cartridge 11 is disposed in a cartridge retainer 14 having a threaded proximal end 13 and an opposed distal end 15.

Medication delivery pen 10 also includes a pen body 12 used to set a desired dose of medication to be delivered by medication delivery pen 10 and a plunger 22 that selectively drives stopper 19 of cartridge 11 in the distal direction based on the dose set by a dose setting mechanism within pen body 12. The dose setting mechanism determines the distance through which plunger 22 and stopper 19 are to be moved during the injection of medication by medication delivery pen 10. Pen body 12 includes an array of threads 21 for threaded engagement with threaded proximal end 13 of cartridge retainer 14 and cartridge retainer 14 includes a set of threads 20 that are used to attach to adaptor and pen needle assembly 16. FIG. 1 also shows a cap 17 that attaches to cartridge retainer 14 to cover adaptor and pen needle assembly 16 between injections.

Figure 2:
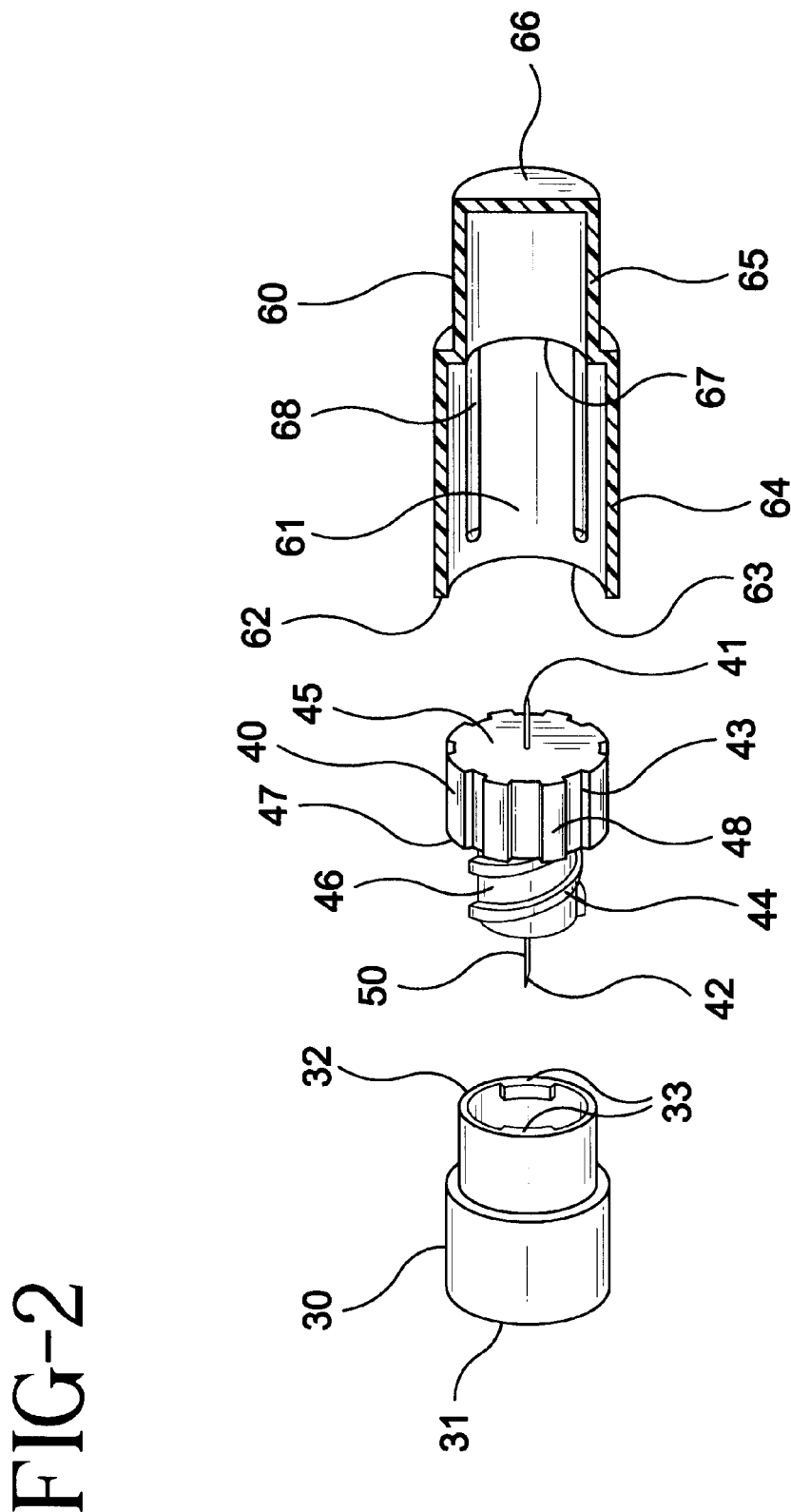
FIG. 2 is an exploded perspective view showing the adaptor, pen needle and a cross-sectional view of a needle holder according to the present invention.
Figure 3:
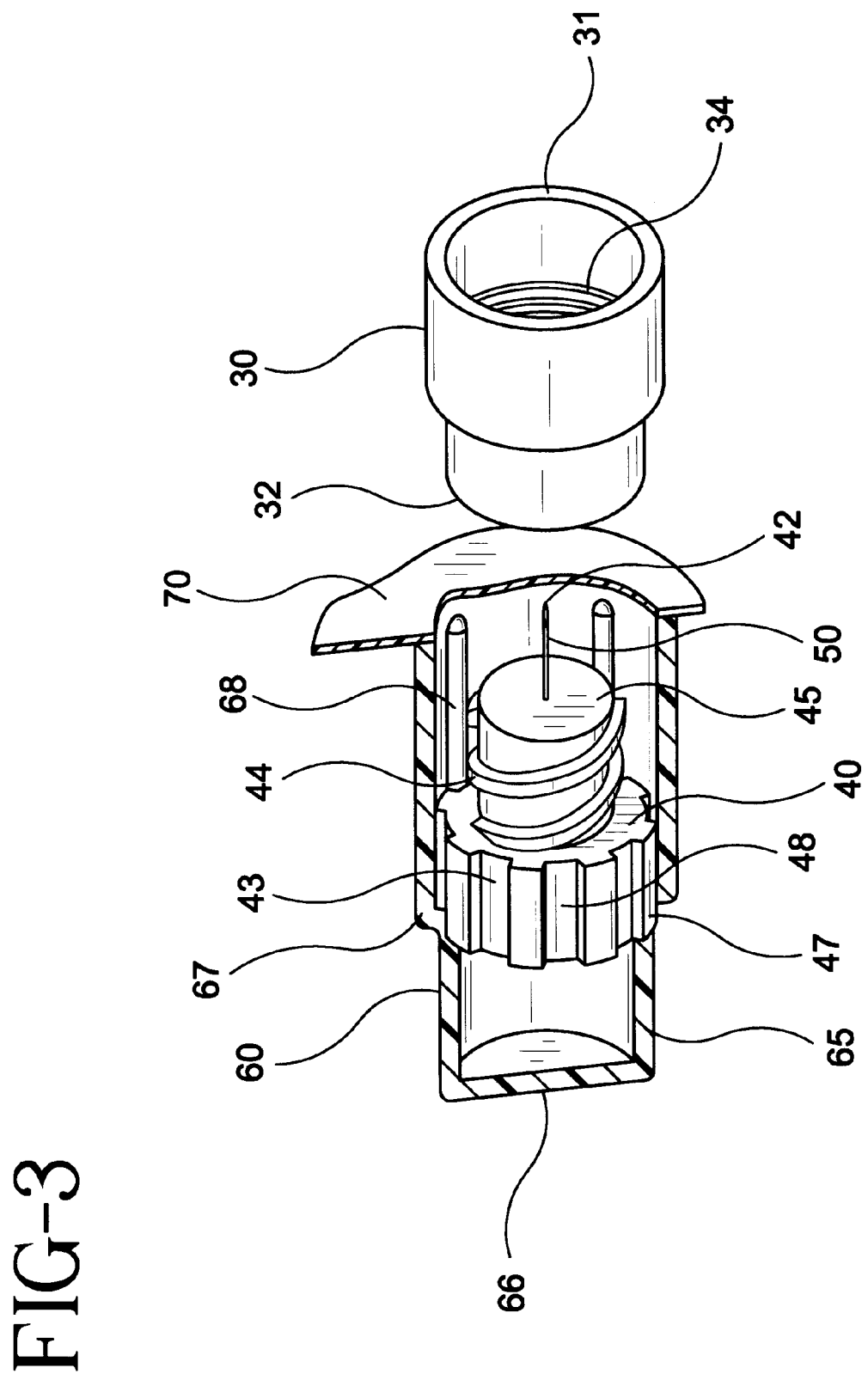
FIG. 3 is a perspective and partial cross-sectional view of the pen needle originally mounted in the needle holder.
Figure 4:
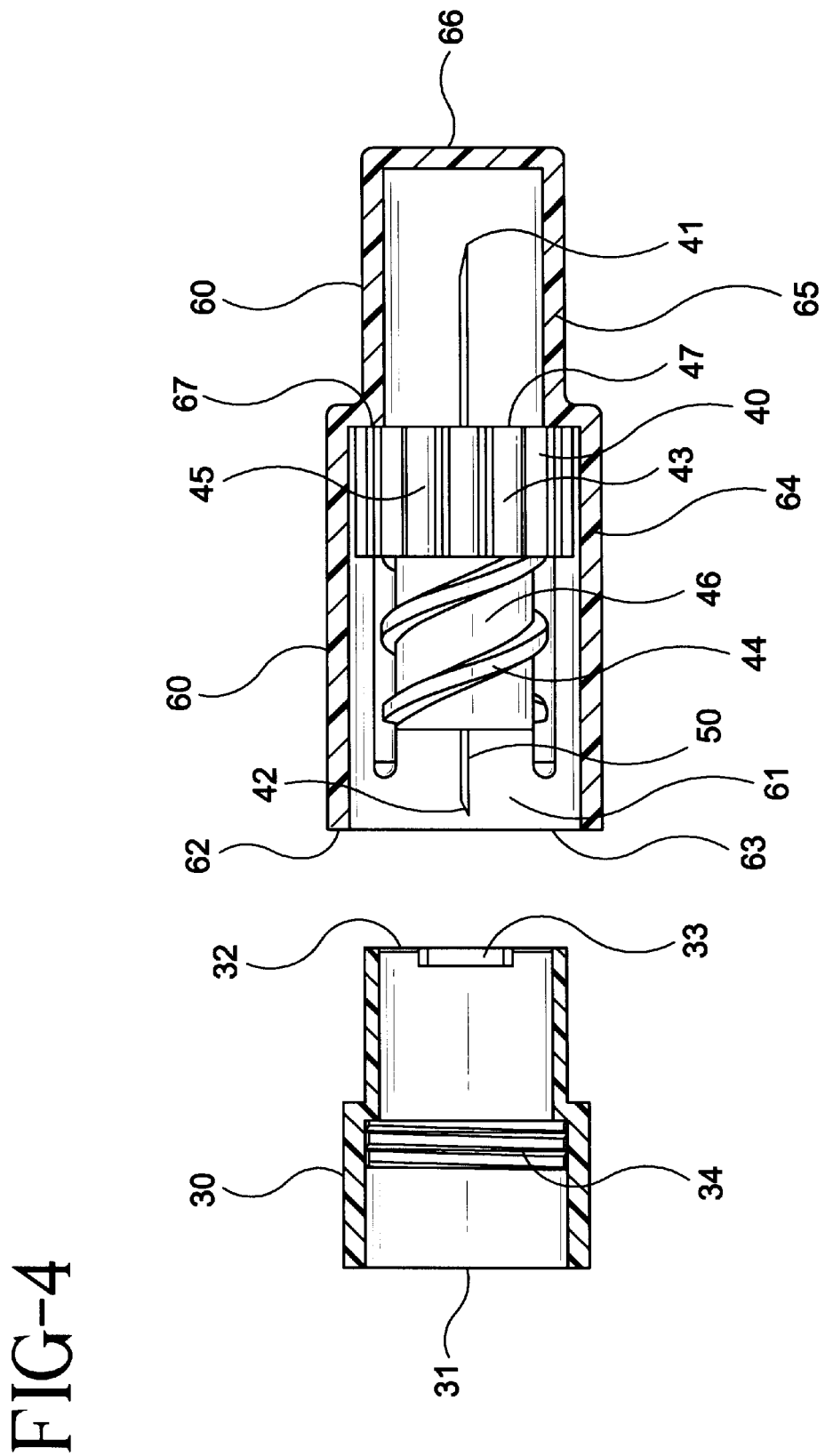
FIG. 4 is a partial cross-sectional view of the adaptor and the pen needle originally mounted in the needle holder as shown in FIG. 3.

FIG. 2 is an exploded perspective view showing an adaptor 30, a pen needle 40 and a cross-sectional view of a needle holder 60, according to the present invention. FIG. 3 is a perspective and partial cross-sectional view showing pen needle 40 originally mounted within needle holder 60 and sealed therein by a sterility barrier or label 70. FIG. 4 is a partial cross-sectional view of adaptor 30 and pen needle 40 originally mounted in needle holder 60, as shown in FIG. 3.

As shown in FIGS. 2–4, adaptor 30 includes an open proximal end 31 designed to be mounted on cartridge retainer 14 and an open distal end 32 designed to receive pen needle 40. Proximal end 31 includes a set of threads 34 that engage threads 20 on cartridge retainer 14 and distal end 32 includes a pair of lugs 33 that mate in a reverse Luer-lock manner with pen needle 40. Alternatively, adaptor 30 can be permanently mounted on cartridge retainer 14 or integrally molded into cartridge retainer 14 so that only pen needles according to the present invention can be attached to distal end 15 of cartridge retainer 14.

Pen needle assembly 16 is more clearly shown in FIGS. 2–4, and includes needle holder 60 and pen needle 40. Needle holder 60 includes a cavity 61 dimensioned to receive pen needle 40, which is described further below. As shown in FIG. 3, pen needle 40 is originally sealed in cavity 61 by a sterility barrier 70 that is attached to a proximal surface 62 of needle holder 60. Sterility barrier 70 provides sterility for unused pen needle 40 contained in cavity 61 and a simple means for the user to identify whether pen needle 40 has been used. Cavity 61 includes an open end 63 leading to an upper section 64 and a bottom section 65 leading to a closed end 66.

As shown in FIGS. 2–4, pen needle 40 includes a cylindrical hub 45 having a proximal section 46 and a distal section 48, with proximal section 46 having one or more threads 44 thereon that mate in a Luer-lock arrangement with lugs 33 on distal end 32 of adaptor 30. Distal section 48 has a larger circumference than proximal section 46 and includes a plurality of laterally extending splines 43 around its circumference that mate with a plurality of splines 68 within cavity 61. A needle cannula 50 is mounted within hub 45 and includes a distal point 41 and a proximal point 42, wherein proximal point 42 extends from proximal section 46 of hub 45 and distal point 41 extends out of distal section 48 of hub 45.

As shown in FIGS. 3 and 4, the plurality of splines 68 on upper section 64 of needle holder 60 mate with the plurality of splines 43 on hub 45 of pen needle 40. The splines 43 and 68 mate to prevent rotational movement between pen needle 40 and needle holder 60, when adaptor 30 is inserted and rotated within cavity 61 to attach or detach pen needle 40 to adaptor 30. By preventing rotation of pen needle 40 within cavity 61 of needle holder 60, the full torque caused by the rotation of adaptor 30 is applied to thread 44 onto the pair of lugs 33 within adaptor 30, when mounting pen needle 40 into adaptor 30.

FIGS. 3 and 4 also shows that bottom section 65 of cavity 61 has a smaller diameter than upper section 64 and together form a shelf 67 where sections 65 and 64 meet. Shelf 67 is used to stop pen needle 40 when it is fully received within cavity 61 of needle holder 60. When pen needle 40 is fully received within cavity 61, bottom section 65 receives distal point 41 on pen needle 40 and proximal point of pen needle 40 is fully surround by upper section 64 to prevent an accidental needle stick by proximal point 42 and permit sterility barrier 70 to be attached to proximal surface 62.

Figure 5:
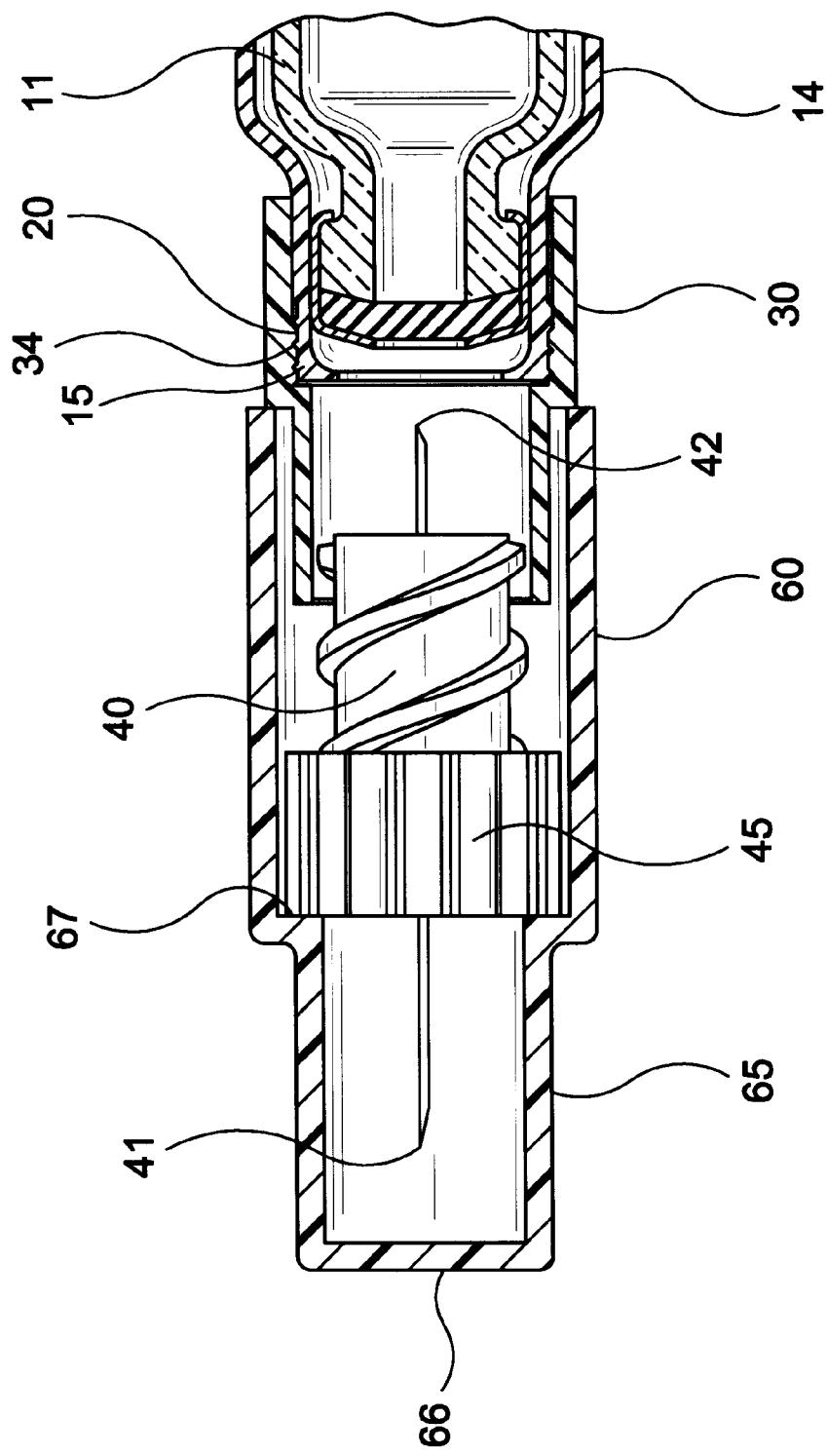
FIG. 5 is a partial cross-sectional view of the adaptor inserted in the needle holder, but prior to being attached to the pen needle.
Figure 6:
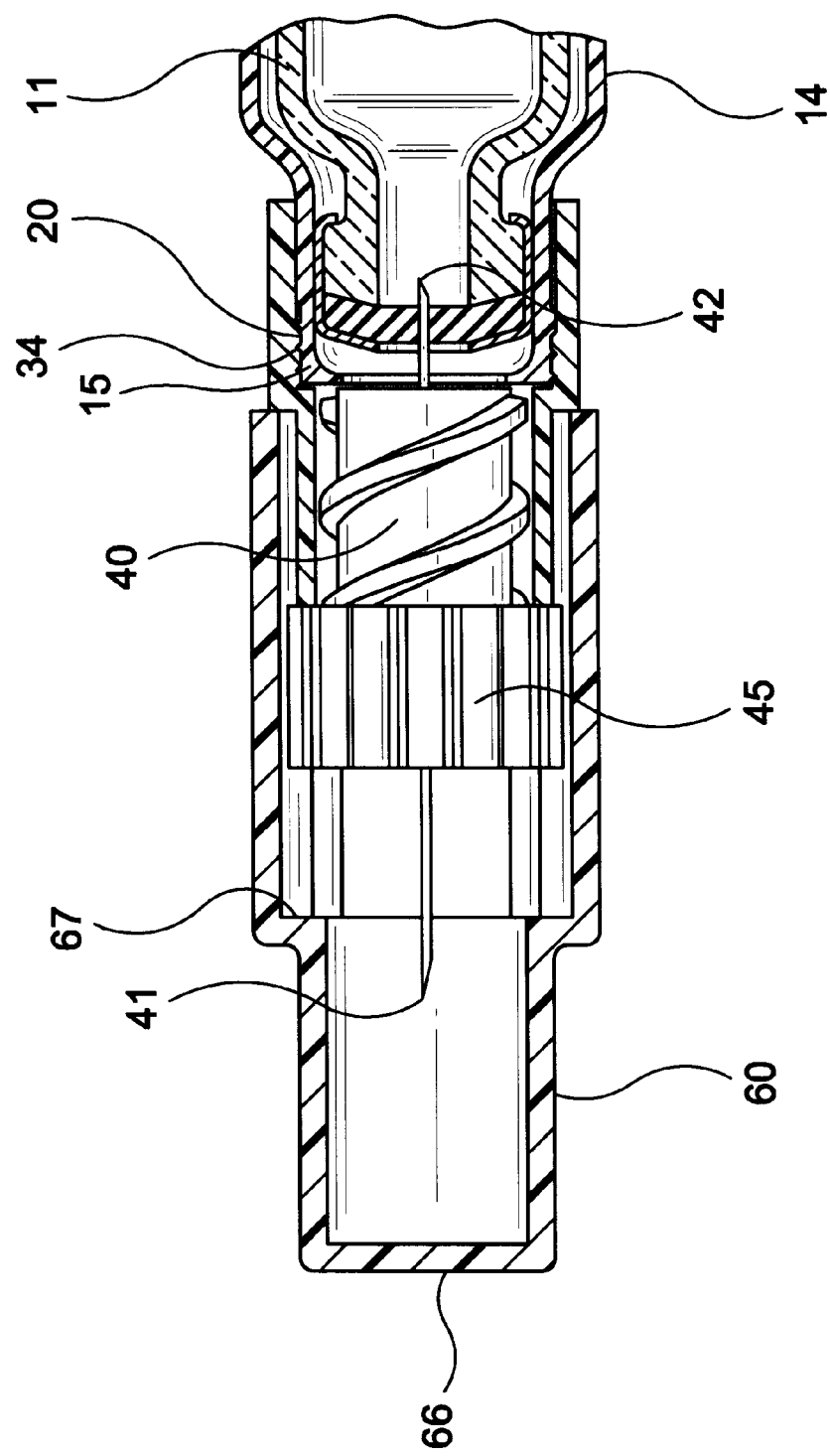
FIG. 6 is a partial cross-sectional view of the adaptor attached to the pen needle.

Pursuant to the present invention, after sterility barrier 70 has been removed, pen needle 40 within cavity 61 of needle holder 60 can be accessed, removed and mounted on the distal end of medication delivery pen 10 using adaptor 30, as shown in FIGS. 5 and 6. FIG. 5 is a partial cross-sectional view showing adaptor 30 mounted on cartridge retainer 20 and inserted in cavity 61 of needle holder 60, prior to being attached to pen needle 40 and FIG. 6 is a partial cross-sectional view showing adaptor 30 attached to pen needle 40. In the present invention, pen needle 40 cannot be removed from cavity 61 unless adaptor 30 is used or a medication pen 10 having a cartridge retainer 14 with a distal end 15 having the dimensions and lugs 33 of adaptor 30 is used. This prevents pen needle 40 from being accidentally removed from cavity 61.

For example, as shown in FIGS. 5–6, adaptor 30 includes a set of threads 34 in open proximal end 31 that are dimensioned to mate with threads 20 on distal end 15 of cartridge retainer 14 and includes a unique pair of lugs 33 extending into open distal end 32. After adaptor 30 has been threaded onto distal end 15 of cartridge retainer 14, distal end 32 of adaptor 30 is used to remove pen needle 40 from cavity 61 by threading the pair of lugs 33 onto the threads 44 on proximal section 46 of hub 45 on pen needle 40. When the lugs 33 are at the base of threads 44 on proximal section 46, rotation of pen body 12 and cartridge retainer 14 causes adaptor 30 to rotate into cavity 61 and thread lugs 33 onto threads 44. In addition, as pen body 12 is rotated and pen needle 40 is threaded into adaptor 30, proximal point 42 of pen needle 40 pierces rubber septum 18 of cartridge 11 in cartridge retainer 14 to place needle cannula 50 in communication with medication contained within cartridge 11.

After use, the used pen needle 40 mounted on adaptor 30 on medication delivery pen 10 is reinserted into cavity 61 until splines 43 on distal section 48 of hub 45 mate with splines 68 within cavity 61. Medication delivery pen 10 is then rotated in the opposite direction to unthread pen needle 40 from adaptor 30 and back into cavity 61. When pen needle 40 contacts shelf 67 in cavity 61, pen needle 40 is fully unthreaded from adaptor 30 and medication delivery pen 10 is then used to pull adaptor 30 out of cavity 61 leaving pen needle 40 in cavity 61 and fully received within needle holder 60.

While the invention has been described with respect to a preferred embodiment, it is apparent that various changes can be made without departing from the scope of the invention as defined by the appended claims.

What is claimed is:

1. A needle assembly for use with a medication delivery pen, said needle assembly comprising:
    a pen needle having:
        a hub;
        means on said hub for attaching said hub to a medication delivery pen; and
        a cannula mounted within said hub and having a distal point and a proximal point;
    an adaptor that receives said pen needle and includes a set of threads for attaching said adaptor to the medication delivery pen; and
    a needle holder having a cavity for fully receiving said pen needle to surround and shield said distal and proximal points of said pen needle from contact.

2. A needle assembly according to claim 1, wherein said attaching means includes a thread on said hub of said pen needle that mates with a pair of lugs on said adaptor.

3. A needle assembly according to claim 2, wherein said proximal point of said cannula extends out of said hub such that when said thread on said pen needle is fully mated to said pair of lugs on said adaptor, said proximal point extends into the medication delivery pen a sufficient distance to pierce a septum within the medication delivery pen.

4. A needle assembly according to claim 1, further comprising means for preventing said pen needle from rotating when said pen needle is received in said cavity of said needle holder to prevent said pen needle from rotating in said cavity as said hub of said pen needle is mounted on said adaptor.

5. A needle assembly according to claim 4, wherein said means for preventing rotation includes a set of splines on said hub of said pen needle that mate with a matching set of splines in said cavity of said needle holder.

6. A needle assembly according to claim 4, wherein said attaching means includes a thread on said hub of said pen needle that mates with a pair of lugs on said adaptor.

7. A needle assembly according to claim 6, wherein said proximal point of said cannula extends out of said hub such that when said thread on said pen needle is fully mated to said pair of lugs on said adaptor, said proximal point extends into the medication delivery pen a sufficient distance to pierce a septum within the medication delivery pen.

8. A needle assembly according to claim 1, wherein said means for attaching said hub to said adaptor is a Luer-lock.

\* \* \* \* \*